United States Patent
Melzer et al.

(12) 
(10) Patent No.: US 6,280,385 B1
(45) Date of Patent: Aug. 28, 2001

(54) STENT AND MR IMAGING PROCESS FOR THE IMAGING AND THE DETERMINATION OF THE POSITION OF A STENT

(75) Inventors: Andreas Melzer, Duisburg; Martin Busch, Witten, both of (DE)

(73) Assignee: Simag GmbH, Berlin (DE)

(*) Notice: Subject to any disclaimer, the term of this patent is extended or adjusted under 35 U.S.C. 154(b) by 0 days.

(21) Appl. No.: 09/172,115

(22) Filed: Oct. 13, 1998

(30) Foreign Application Priority Data

Oct. 13, 1997 (DE) .............................................. 197 46 735

(51) Int. Cl.[7] .............................. A61B 5/055; A61B 17/00
(52) U.S. Cl. ............................................. 600/423; 324/318
(58) Field of Search ..................................... 600/410, 423, 600/419, 424; 324/309, 306, 318

(56) References Cited

U.S. PATENT DOCUMENTS

| | | | |
|---|---|---|---|
| 4,960,106 | 10/1990 | Kubokawa et al. | 128/6 |
| 5,160,890 | 11/1992 | Roschmann | 324/314 |
| 5,170,789 | 12/1992 | Narayan et al. | 128/653.5 |
| 5,445,151 | 8/1995 | Darrow et al. | 128/653.3 |

FOREIGN PATENT DOCUMENTS

| | | |
|---|---|---|
| 4008202 | 9/1991 | (DE) . |
| 42 38 831 A1 | 5/1994 | (DE) . |
| 4238831 | 5/1994 | (DE) . |
| 195 10 194 A1 | 10/1995 | (DE) . |
| 195 07 617A1 | 9/1996 | (DE) . |
| 0 597 546 A1 | 5/1994 | (EP) . |
| 0 602 970 A2 | 6/1994 | (EP) . |
| 0 673 621 A1 | 9/1995 | (EP) . |
| 0-A2768539 | 4/1997 | (EP) . |
| 0-A3768539 | 4/1997 | (EP) . |
| 0-A1775500 | 5/1997 | (EP) . |
| WO9638083 | 12/1996 | (WO) . |

OTHER PUBLICATIONS

M. Burl, G.A. Coutts, I.R. Young Tuned Fiducial Markers to Identify Body Locations with Minimal Perturbation of Tissue Magnetization, *Journal of Magnetic Resonance in Medicine*, 1996, pp. 491, 492, 493.

J. Tanttu Floating Surface Coils, *XIV ICMBE and VII ICMP*, Espoo, Finland, 1985.

International Preliminary Examination Report—Supplement with WIPO translation; Jan. 21, 2000.

*Primary Examiner*—Peter Vo
*Assistant Examiner*—Shawna J. Shaw
(74) *Attorney, Agent, or Firm*—Christie, Parker & Hale, LLP

(57) ABSTRACT

The invention relates to a magnetic resonance imaging process for the imaging and determination of the position of a stent introduced into an examination object as well as to the stent so utilized. According to the invention, the stent has at least one passive resonance circuit with an inductance and a capacitance whereby its resonance frequency is essentially equal to the resonance frequency of the applied high-frequency radiation of the magnetic resonance system. A changed signal response is thus produced in a locally defined area in or around the stent which is imaged in spatial resolution.

71 Claims, 8 Drawing Sheets

STENT AND MR IMAGING PROCESS FOR THE IMAGING AND THE DETERMINATION OF THE POSITION OF A STENT

FIELD OF INVENTION

The present invention relates generally to magnetic resonance imaging (MRI). The present invention relates more particularly to a stent and an MRI process for the imaging and determination of the position of the stent as the stent is being introduced into an object to be examined.

BACKGROUND OF THE INVENTION

Magnetic resonance imaging processes have been known for some time. They are based on the resonance alternating effect between an alternating high-frequency electromagnetic field and specific atomic nuclei of an object to be examined, e.g., a human or an animal body, that is disposed in a strong external magnetic field. The atomic nuclei precess in the magnetic field ($B_o$) by the so-called Lamor frequency in a manner which is proportional to the strength of the field. When applying an electromagnetic alternating field whose magnetic alternating component ($B_1$) is vertical to the direction of the strong magnetic field ($B_o$), the spins of the atomic nuclei flip and connected relaxation times may thus be measured.

In the description of a scientific model, the magnetization of the individual spins is described by total magnetization. This total magnetization in its equilibrium condition is parallel to the external magnetic field and is called equilibrium magnetization. By means of an HF-impulse applied with the Lamor frequency (resonance frequency), the magnetization may be deflected by an angle $\alpha$ with regard to the direction of the magnetic field. The angle $\alpha$ is proportional to the time period of the HF-impulse applied and the strength of the magnetic field ($B_1$) of the HF-impulse. Subsequent to an excitation by the angle $\alpha$, the total magnetization precesses by the direction of the magnetic field. The precessing magnetization may be recorded by a coil that is oriented vertically to the direction of the magnetic field in form of a voltage signal. The strength of the voltage signal is directly proportional to $\sin(\alpha)$, directly proportional to the density of the spins in the signal emitting volume and inversely proportional to the temperature.

The maximal signal response of a given volume is thus attained after 90° excitation. The recorded signal amplitude decreases exponentially with the relaxation time $T_2^*$, since the individual spins fall out of phase due to the fluctuating magnetic fields. Simultaneously, the total magnetization increases exponentially again in the direction of the magnetic field towards the equilibrium magnetization with relaxation time $T_1$. By means of magnetic gradient fields switched at the correct point in time, it is possible to image differentiated combinations from the spin density and the two relaxation times in a gray scale encoded image with spatial resolution.

It is further known to locally induce an amplification of the excitation of the nuclear spins by means of a resonance circuit. For this, so called "fiducial markers" are known that have compartments with special signal-intensive liquids surrounded by a resonance circuit. (Burl et al.: "Tuned Fiducial Markers To Identify Body Locations with Minimal Perturbation of Tissue Magnetization", in: Journal of Magnetic Resonance in Medicine 1996, p. 461–493.) The resonance circuit has the resonance frequency of the magnetic resonance system.

If such a fiducial marker is brought into the imaging volume of a nuclear magnetic resonance tomograph, the resonance circuit is excited when electromagnetic radiation is applied at resonance frequency. This results in the amplification of the magnetic alternating field within the inductance of the resonance circuit. The increased magnetic component of the magnetic field increases the deflection angle $\alpha$ of the protons within the inductance. With such a small angle of excitation ($\alpha<90°$) of the protons by the nuclear spin system, the protons experience an increased excitation angle within the inductance. In the ideal case, protons are excited with a small angle of 1° to 10° in the imaging volume, whereas the protons within the inductance are excited with 90°. Even with identical relaxation times and with an identical spin density, the signal from the compartment surrounding the resonance circuit is clearly more intensive than the signal of the other parts of the image. Since this signal amplification is localized, it may be used for the determination of positions.

According to the law of reciprocity, it is equally true that the magnetic resonance response signals of the protons within the compartment surrounding the resonance circuit (fiducial markers) are amplified. Due to the inductance, the magnetic field lines originating from the spins within the coil are bundled such that more signal is emitted from the volume within the inductance and applied to a corresponding receptor coil. This amplification of emitted and then received signals is considered independent of an increased excitation. Both effects result in a changed signal response of the fiducial marker.

Disadvantageously, fiducial markers make use of separated signal emitting volumes, which for visibility in the magnetic resonance image must be at least a few cubic millimeters in size and which have to be placed specifically in the examination object or which have to be integrated into the systems that are placed in the examination object. Often this is not possible.

With the introduction of open magnets and new techniques with closed magnetic resonance systems it has become possible to carry out interventional and minimally invasive techniques such as punction, catherization and surgical processes under magnetic resonance tomographic control. However, ferromagnetic or paramagnetic metals or impurities in other materials result in artifacts in the images.

Problems result from the tools used for interventional and minimally invasive techniques since they usually consist of ferromagnetic or paramagnetic material and/or that they are so small that they are about the size of one pixel (approximately 1mm) in magnetic resonance images. In particular, stents made of metal or plastic are barely visible due to their fine skeletons and can best be located by means of artifacts. When materials that are not visible in the magnetic resonance image are used, they can be seen as "shadows" only. These disadvantages result in the fact that magnetic resonance monitoring is frequently unsatisfactory and that an x-ray process with all its known disadvantages is used instead for imaging.

From DE 195-10-194-A1 an active-invasive magnet resonance system for the production of selective magnetic resonance angiograms is known, whereby an invasive apparatus is provided with a high frequency (HF) coil by which the nuclear spin magnetization of the blood flowing in the vessel is changed locally. By means of special magnetic resonance image impulse sequences, only the blood that has a changed nuclear spin magnetization is selectively detected and imaged.

U.S. Pat. No. 5,445,151 describes a process for flow measurements in flowing fluids, in particular in blood, whereby the invasive apparatus is provided with at least two HF coils, whereby a local change in nuclear spin magnetization produced by one HF coil is sensed at the other HF coil and the delay interval is used for the computation of flow velocity.

The two publications cited do not refer to the imaging of medical apparatus introduced into a body. Furthermore, they have the disadvantage that they are active systems whereby the apparatuses introduced are permanently connected via cable connections to extracorporeal components.

Patent publication DE 195-07-617-A1 describes an magnetic resonance process whereby a surgical instrument, such as a catheter, is introduced into the examination object, whereby the catheter is provided with a micro-coil at its point. The position of the micro-coil is determined by specific sequential techniques.

OBJECT OF THE INVENTION

The object of the present invention is to provide a magnetic resonance imaging process for the imaging and the determination of the position of a stent introduced into an examination object and to provide a stent which allows for clear, signal-intensive imaging of the stent in magnetic resonance images, as well as for improved fluid flow measurements.

SUMMARY OF THE INVENTION

These and other objects are achieved by the present invention, which comprises a stent which is to be introduced into the examination object. The stent is provided with an integrated resonance circuit which induces a changed response signal in a locally defined area in or around the stent that is imaged by spatial resolution. The resonance frequency is essentially equal to the resonance frequency of the applied high-frequency radiation of the magnetic resonance imaging system. Since that area is immediately adjacent to the stent (either inside or outside thereof), the position of the stent is clearly recognizable in the correspondingly enhanced area in the magnetic resonance image. Because a changed signal response of the examined object is induced by itself, only those artifacts can appear that are produced by the material of the stent itself.

Due to a clear imaging of the stent in the magnetic resonance image, a precise position determination is possible. Furthermore, based on the changed signal conditions, improved flow measurement of the medium flowing through the stent or along the stent is now possible. Use is made of the fact that different excitation is present inside and outside the stent.

The present invention is based on the surprising discovery that suitable resonance circuits can be provided or disposed on a stent itself. Advantageously, the present invention preferably provides that the inductor and capacitor defining the resonance circuit are formed by the material of the stent, thereby resulting in an additional synergistic effect. It is also within the framework of this invention to form the inductor and capacitor as separate components on the stent.

According to the invention, the signal response of the spins within the inductance is changed. Two processes contribute to this. On the one hand, the resonance circuit tuned to the resonance frequency is excited by the application of high-frequency radiation and the nuclear spins detected by the field of the resonance circuit experience amplified excitation through the local amplification of the alternating magnetic field in or near the inductance. In other words, protons detected by the field lines of the induced magnetic field are deflected at a larger angle than the protons on the outside of this induced magnetic field. An increased flip of the nuclear spins results. Accordingly, the signal response sensed by a receptor coil and evaluated for imaging can be amplified. It is furthermore possible that only the spins within the inductance experience saturation and that the signal is diminished with regard to the environment. In both cases, a change in signal response is apparent.

On the other hand—independent of amplified excitation—the magnetic resonance response signals of the protons within the inductance are amplified. The inductance thus bundles the magnetic field lines originating from the spins within the inductance, which results in an amplified signal emission and an application to a corresponding receptor coil that receives the amplified signals and transmits them for magnetic resonance imaging. This effect is described in the publication by J. Tanttu: "Floating Surface Coils", in: XIV ICMBE and VII ICMP, Espoo, Finland 1985".

According to the present invention, both of these effects may be used in the process of changing the signal response. However, the second effect, that is, an amplification of the magnetic resonance response signal, may also be used alone.

Accordingly, a first embodiment of the present invention is characterized in that the application of high-frequency radiation excites the resonance circuit, thus resulting in an amplified excitation of the nuclear spins in the locally defined area. Preferably, the locally defined area in which such an amplified excitation of the nuclear spins take places is located within the stent. This is obviously the case if the skeleton of the stent forms the inductance.

A second embodiment of the invention, however, provides, that with the application of the high-frequency radiation the resonance circuit becomes detuned or that the capacitor is short circuited to the extent that no enhanced excitation of the nuclear spins takes place in the locally defined area. However, during measurements of the signal response of the locally defined area, the detuning of the resonance circuit, that is, the short circuit of the capacitor is canceled, thus causing the resonance circuit to provide an amplification of the radiated magnetic resonance response signals of the protons. It was in particular found that this variant makes possible the imaging of the area in and around the stent with high quality, that is, that it provides local imaging beyond the pure position determination. In addition to the position of the stent, the magnetic resonance image provides improved information regarding the structure, etc. of the inside and/or the environment of the stent.

An amplification of the excitation of the nuclear spin is, e.g., suppressed, in that the condenser of the resonance circuit is short circuited during excitation by means of crossed diodes. The amplification of the emitted signals is thus not influenced, since the small induced voltage from the spins within the inductance is below the conducting-state voltage during emission.

General reference is made to the fact that the change of the signal response according to the invention will usually be an amplification of the signal response. However, this depends on numerous factors, in particular on the excitation sequences used. For instance, with quick consecutive sequences it is possible that a saturation of the excitation of the spins within the inductance is present, thus no signal is produced there. There is, however, no saturation present in the area outside of the inductance, where a smaller excitation of the nuclear spins takes place, thus a signal is produced here. Correspondingly, in this example, a decrease in the signal response occurs in the area detected by the field of the inductance.

A preferred embodiment of the invention provides that the resonance circuit at the stent is formed or activated after insertion of the stent into the examination object, particularly while unfolding the stent during its application. Preferably, inductor and/or capacitor are hereby adjustable for resonant tuning of the resonance circuit. This makes sense, in particular, if, after application, that is, after unfolding of the stent, the product of inductance and capacitance, and thus the resonance frequency of the resonance circuit, changes.

In an advantageous embodiment of the present invention, at least two resonance circuits are formed or disposed on the stent, whereby the coils of the corresponding inductance are in particular disposed vertically aligned to each other or disposed behind each other. Vertical coils aligned to each other assure that in every arrangement of the stents in the outer magnetic field, one component of the inductance runs vertical to the field direction of the outer magnetic field, such that a changed signal response is assured. In addition, using suitable sequence techniques, coils disposed behind each other are particularly suited to carry out a flow measurement (e.g., determination of velocity) of the medium flowing through or along the stent.

Any type of conventional systems may be used for the magnetic resonance imaging system.

In the stent according to the present invention, inductance is preferably formed by the material, that is, the skeleton of the stent. Additional parts are thus avoided and the inductance is formed simply and automatically by unfolding of the stent during application.

The stent thus preferably consists of a material that has at least one layer of high conductivity forming the inductance and one other layer with low conductivity forming the skeleton for the actual stent function. The layer with high conductivity is cut at suitable locations to thus form various areas of the skeleton that are insulated from each other, thus forming an inductance.

Alternatively, the inductor of the resonance circuit is formed by a separate coil that is integrated into the stent skeleton. For instance, the coil is woven, knitted, welded, soldered or glued into the skeleton of the stent. The coil is preferably connected with the skeleton such that it unfolds with the unfolding of the stent either self-expanding elastically or remote expanding plastically or thermally induced.

The skeleton of the stent is provided preferably in form of a helix, a double helix or multiple helix, as a metal frame or as knitted, cut, or etched sheet metal or pipe.

Preferably, the capacitor of the stent is at least partially also formed from the stent material, in particular by parallel wires or surfaces of the inductance. Corresponding surfaces may be formed by the production of the stent. The capacitor may generally be formed as a dielectric by means of suitable arrangements of the conducting layers and a material such as the stent skeleton. With corresponding geometry of the elements forming the capacitor, the implantation tissue may also serve as a dielectric.

Alternatively, provision is made to form the capacitor of the stent by means of a separately provided capacitor that is connected to the body of the stent.

Preferably, the apparatus according to the present invention is formed in such a way that with a change in the geometry of the apparatus during application, for instance, by a widening of the stent, the product of inductance and capacitance of the resonance circuit, in particular an increase in inductance with a decrease in capacitance or vice versa remains essentially constant. This guarantees that the resonance frequency remains essentially unchanged.

BRIEF DESCRIPTION OF THE DRAWINGS

These, and other features, aspects and advantages of the present invention will be more fully understood when considered with respect to the following detailed description, appended claims and accompanying drawings, wherein:

FIG. 5 shows a section through the stent material of FIG. 4a;

DETAILED DESCRIPTION OF THE PREFERRED EMBODIMENTS

The detailed description set forth below in connection with the appended drawings is intended as description of the presently preferred embodiments of the invention and is not intended to represent the only forms in which the present invention may be constructed or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

Figure 1:
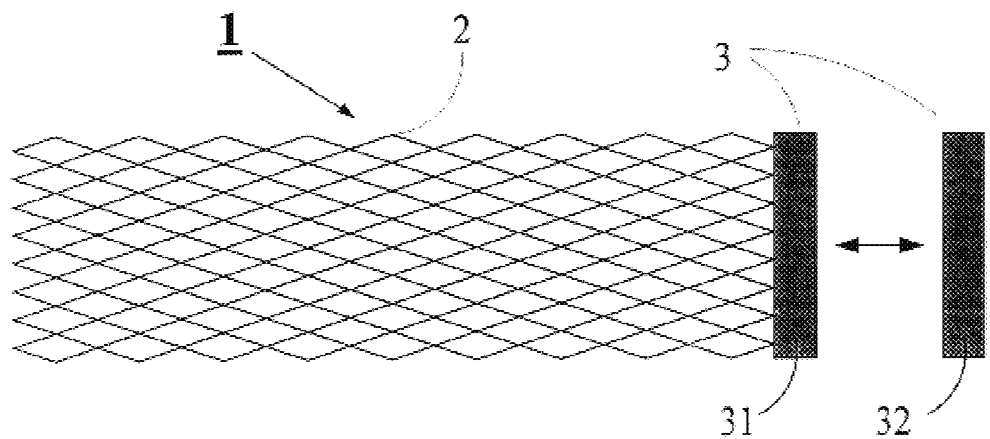
FIG. 1 schematically shows a stent according to the present invention wherein the stent forms a resonance circuit with an inductor and a capacitor.

Referring now to FIG. 1, a stent 1 according to the present invention, may, for instance, be comprised of metals such as platinum, titanium or titanium alloys and compounds, or of plastics or carbon fibers. The area of application of such stents is particularly the bridging of narrow areas such as those due to tumors, as well as otherwise narrow areas (e.g., in the gastro-intestinal and bronchial tract) in internal organs, arterial and venous vessels, vascular strictures, peripheral and central vascular stenosis and in particular in coronary heart disorders. Further applications are the creation of new vascular passages (shunts) in organs, e.g., in the liver.

The stent effects a mechanical sealing and a permanent widening of the corresponding region and leaves a smooth surface with improved blood flow, enlarging the vascular volume and decreasing the recurrence of occlusions that frequently occur after conventional balloon dilation.

However, the success rate of stents is limited, since in the area of the skeleton, reocclusions, such as those caused by growing tumor tissue or by blood clots (so called thromboses), may occur and acutely close the lumen. Due to luxuriant tissue touching the skeleton, new arteriosclerotic deposits may occur and occlude the lumen of the stent again. Follow-up examination of the stent function is of utmost importance because clinical symptoms occur only with narrowings of a higher degree. However, this depends on the degree of the occlusion and thus the risk of an acute occlusion through thromboses. However, to date, this is possible only with the invasive catherization of the corresponding vessel, the use of allergenic kidney stressing contrast medium and x-ray techniques. Based on the definite susceptibility of artifacts caused by state of the art stents, a magnetic resonance check-up is virtually impossible. Ultrasound examination are also very limited due to the distinctive formation of sound echos from the stent skeleton. So far the inside of the stent is beyond any form of medical diagnostic imaging.

Stents usually consist of metal skeletons, e.g., continuous metal wires or a type of mesh tube or they are produced from metal pipes by means of laser or spark erosion techniques. Within the framework of this application we use the term "skeleton" for all these stent embodiments. For insertion, a stent is, for example, put onto a balloon catheter and placed at the implantation location by means of a catheter and then unfolded whereby the diameter of the balloon increases the diameter of the stent, pushing it against the wall of the vessel. In addition to balloon expanded plastically deformable stents, self-expanding elastic or thermally expanding stents are also known.

Due to their metallic structure, known stents can not be imaged in a magnetic resonance image. Contemporary stents frequently form distinctive artifacts to the extent that precise placement and monitoring of the placement in a timely process, as well as functional control after the placement, is not assured when using magnetic resonance tomography as an imaging process.

Figure 3:
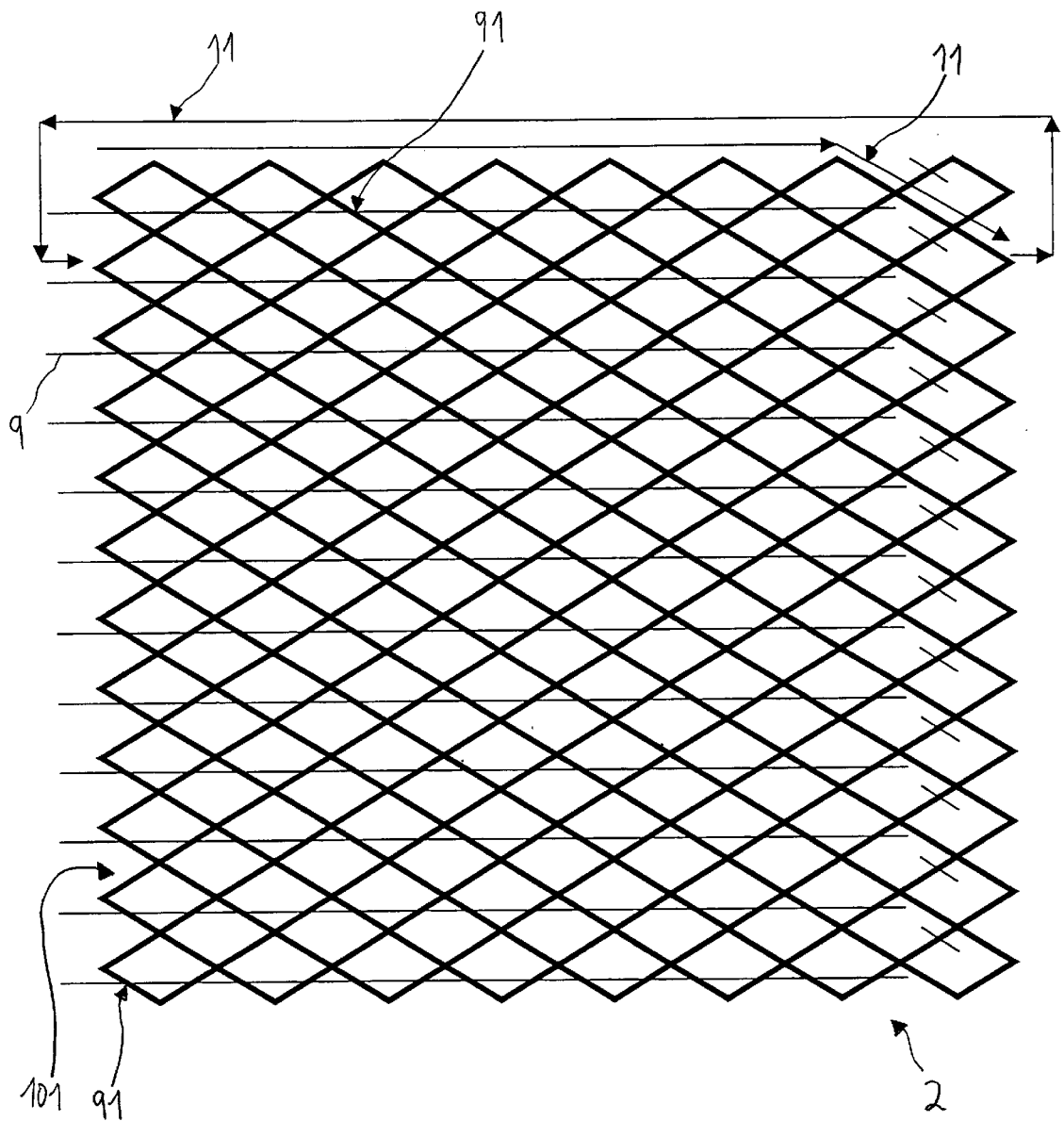
FIG. 3 shows a more precise depiction of the skeleton of the stent.

For improved imaging and functional control of the stent in the magnetic resonance image, the stent 1 according to the present invention and as shown in FIG. 1 is provided with an inductor defined by the skeleton 2 and a capacitor 3. Thus, the inductance of the stent 1 is provided by the skeleton 2 of the of the stent 1. Provision is made that the individual components of the skeleton 2 are insulated relative to each other as shown in FIG. 3. Insulation of the individual components of the skeleton 2 may take place during the manufacturing process, whereby an insulating layer is applied to the skeleton which is formed during separate phases of the manufacturing process of the stent which is made from a metal pipe or tube.

The inductor 2 is electrically connected to the capacitor 3, such that the inductor 2 and capacitor 3 form a resonance circuit. In FIG. 3 the capacitor 3 is provided as a plate capacitor defined by two plates 31 and 32. However, any other desired capacitor may be used. It is within the framework of this invention that the capacitor 3 does not represent an individual component, but that is consists simply of the inductor 2 from the material of the stent 1, e.g., it is formed by parallel wires of the wire skeleton. We may add, that for reasons of clearer depiction, the electrical connection between the capacitor plate 32 and the inductance is not shown in FIG. 1.

Figure 2A:
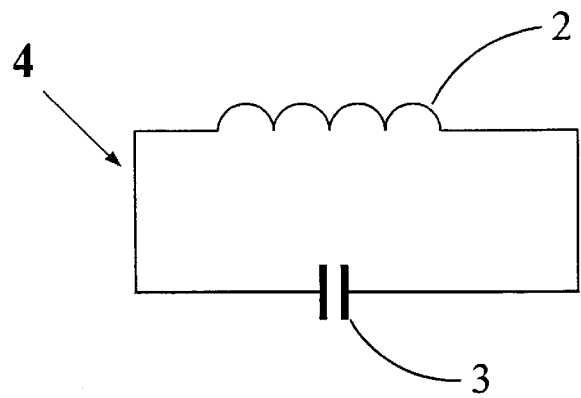
FIGS. 2a–2g shows several electrical diagrams of the apparatus according to the present invention.
Figure 2B:
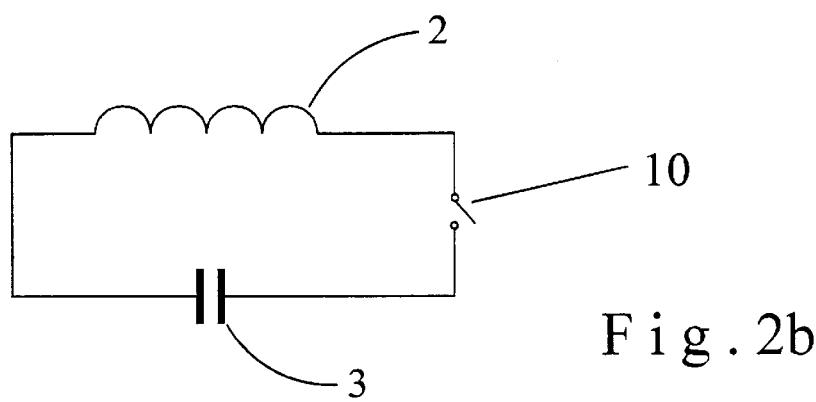

FIG. 2a discloses the electrical diagram of the resonance circuit 4 provided in the stent 1, consisting of inductor 2 and capacitor 3. According to FIG. 2b, an optional additional switch 10 is provided, which can be activated or deactivated electrically or magnetically, for instance, or mechanically by means of a catheter used in the application.

Figure 2C:
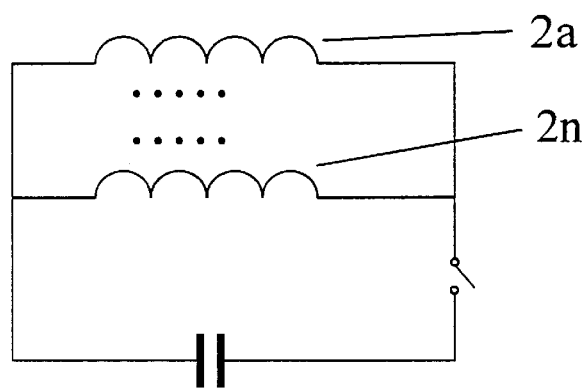
Figure 2D:
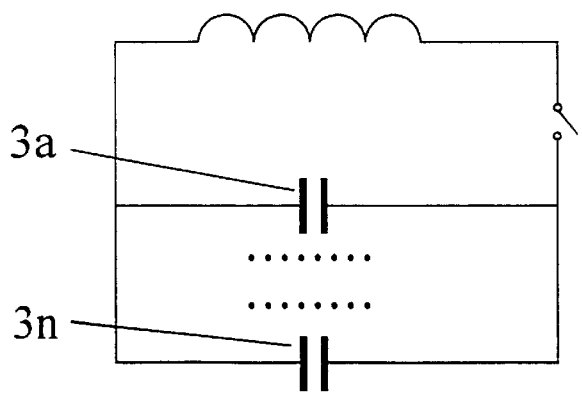

The resonance circuit 4 can be designed in a multitude of embodiments. According to FIG. 2c, it may have several parallel switched inductances 2a to 2n and according to FIG. 2d it may have several parallel switched capacitors 3a to 3n. Furthermore, several inductances and/or capacitances may be serially switched. Several resonance circuits may also be provided on a stent which may each have a switch and may have serially and/or parallel switched inductors and/or capacitors. Especially with several parallel or serially switched inductances, flow measurements may be refined by means of suitable sequences.

The resonance circuit 4 has a resonance frequency that corresponds approximately to the resonance of the high-frequency (HF) radiation utilized in the magnetic resonance imaging system which is used to image the human body into which the stent is inserted.

In the stent 1 according to the present invention, the resonance circuit 4 is excited by the applied high-frequency pulses of the magnetic resonance system, since its resonance frequency corresponds to the frequency of the applied HF-pulse. This results in the amplification of the magnetic field in the inductor of the resonance circuit or near the inductor, which again may result in an amplified excitation of the protons in the corresponding area. In an excitation of the nuclei outside of the inductor resulting in an excitation angle that is smaller than 90°, nuclei within the inductance may experience an excitation of 90° and thus respond at a maximum amplitude. The protons of nuclei disposed in the area of the inductor thus experience a stronger excitation than the protons disposed outside the inductor.

The increase in the deflection angle within the inductor may be as much as 45° as compared to the protons outside the inductor. It is therefore possible to deflect the protons inside the inductor by an angle of 90° (max. signal response), whereas the protons outside the inductor, that is, outside the magnetic field produced by the resonance circuit, experience no more than a small angle excitation of 20 to 10°. Because of this, the inside area of the stent can be imaged essentially brighter in a magnetic resonance image than the rest of the area. Therefore, the location of the stent in the human body can be precisely determined.

Various formations of the resonance circuit 4 are possible for the tuning of the resonance frequency of the resonance circuit 4 to the frequency of the applied HF pulse.

In a first variant of the basic configuration, provision is made that the quality (Q factor) of the resonance circuit is kept relatively low in order to form a resonance circuit with the broadest possible bandwidth and thus to cover the largest possible range of resonance frequencies.

A second variant provides an apparatus with the capability to keep the product of inductance and capacitance constant even after a change of the geometry as was observed in the example referring to the unfolding of the stent. This may take place either in that the stent is given a geometry that changes its properties as little as possible after unfolding of the stent. Thus, the stent is provided with a substantially constant inductance and a substantially constant capacitance. A widening of the stent at the implantation location thus essentially effects substantially no change in the resonance of the resonance circuit.

A constancy of the product of inductance and capacitance may be realized, among other things, by a compensation of the changing inductance by a correspondingly changing capacitance. For instance, provision is made that a capacitor surface is enlarged or decreased for compensation of a changing inductance by a correspondingly changing capacitance, such that the capacitance increases or decreases according to the corresponding distance of the capacitor surfaces. The movability of the capacitor plate 32 with regard to the capacitor plate 31 and the adjustability of the capacitance thereby is schematically shown in FIG. 1 by a double arrow.

A third variant discloses that an adjustment of the resonance circuit in the magnetic field of the nuclear spin tomograph is induced by a change or adjustment of the inductor and/or the capacitor of the resonance circuit after their placement. For example, a change of the capacitor surface is provided by means of the application instrument located in the body, such as a catheter. A decrease in the inductance and thus an adjustment of the resonance circuit to the resonance frequency in the nuclear spin tomograph may take place, for instance, by a laser induced mechanical or electrolytic insulation of coil segments. A change in the capacitor may also take place by a laser induced mechanical or electrolytic insulation of the capacitor.

FIG. 3 schematically discloses a possible embodiment of a stent according to FIG. 1. According to FIGS. 4a and 4b, the stent material consists of two (FIG. 4a) or more (FIG. 4b) layers 81 and 82. The first layer 81 depicts the material for the actual stent function. It has poor conductivity and a high level of stability and elasticity. Suitable materials are mainly nickel-titanium, plastic or carbon fibers. The additional layer(s) 82 provide the material for the formation of the inductor. The layer 82 has a very high conductivity. Suitable materials are gold, silver or platinum which, in addition to their high level of conductivity, are also characterized by their biocompatibility. When using less biocompatible electric conductors such as copper, a suitable plastic or ceramic coating may achieve the desired electrical insulation and biocompatibility.

Figure 4A:
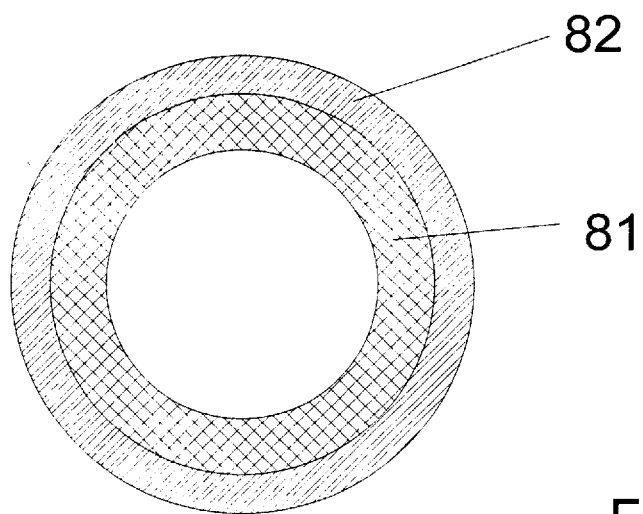
FIGS. 4a–4b shows two examples for the construction of the stent material.
Figure 4B:
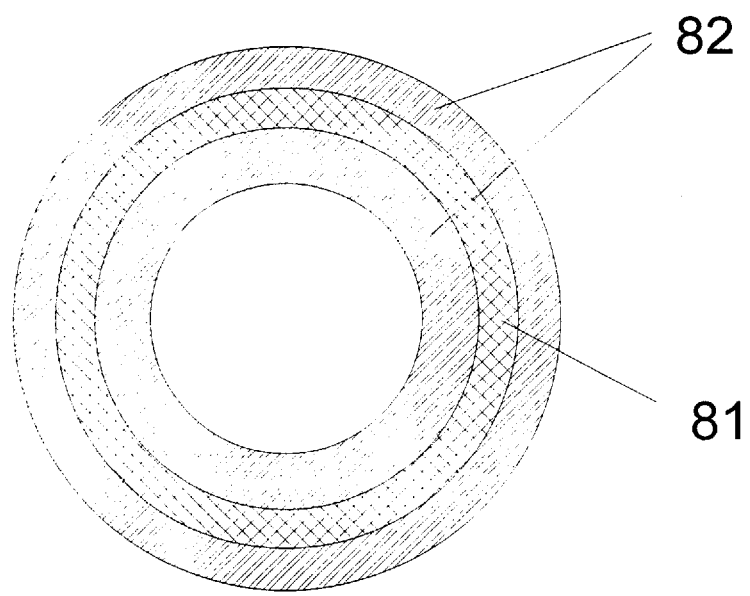

The manufacture of the stent material according to FIGS. 4a and 4b takes place, for example, using a pipe made of titanium or titanium alloys or compounds coated with the material for the formation of an inductor which are consequently cut by known laser or spark erosion or water torch techniques.

Figure 5:
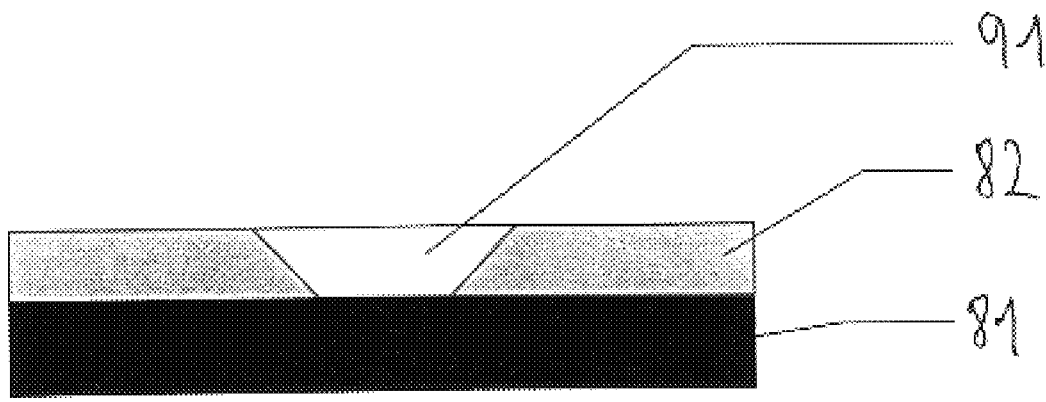

According to FIG. 3, a coil with the material of FIG. 4a is formed as follows. The stent 1 consist of a two layered material that forms a honey-comb structure 101 and may, e.g., be cut from a pipe by means of laser cutting techniques. FIG. 3 shows the pipe folded apart. Thus, the left and the right side are identical. The conductive layer of the honey-comb structure is interrupted along the lines 9. For this purpose the conductive layer is cut during manufacture of the stent after the formation of the structure at the corresponding locations 91 by means of a chemical, physical or mechanical process. Such a location 91 where the conductive layer 82 disposed on the actual stent material is interrupted is schematically shown in FIG. 5.

By the separation locations 91, the current path through the conductive material 82 is defined as it is indicated (by arrows 11) in FIG. 3. A coil arrangement 2 is created that forms the inductance of the stent 1. Conductive material for the coil function is selected in that the resistance through the conductor formed by the conductive material from one end to the other of the stent is lower than the default resistance through the stent material.

The inductance 2 is formed automatically by the unfolding of the stent material during the application of the stent.

When using a three layered material according to FIG. 4b, the formation of an inductance takes place in a corresponding manner, whereby the layers of the conductive material are provided with separation locations for the formation of a current path. The use of two conductive layers has the advantage that the cross-section of the conductive track (land) is effectively doubled.

In a further development of the exemplary embodiment of FIGS. 3 to 5, the conductive layer 82 is additionally coated with an insulating plastic such as a pyrolene in order to safely prevent current flow through the adjacent blood that would decrease the inductance of the coil. Pyrolenes are well suited since they are biocompatible and bond quite well with metal alloys. When coating the stent with pyrolenes after the manufacture process, the stent is held in a bath with pyrolenes or vaporized with pyrolenes.

An estimate of the required capacitances and inductances follows for the further disclosure of details of the invention. In the exemplary embodiment a plate condenser is used and the coil is assumed to be a helix with a fixed number of turns. The resonance frequency of nuclear spin systems is usually equal the product of the magnetic field strength and the gyromagnetic relationship g. At a medium field strength of 1 tesla, a resonance frequency of ca. 42 MHz results. The resonance frequency of the resonance circuit results from Thomson's resonance equation. It is inversely proportional to the root of the product of the inductance and the capacitance.

The product of inductance and capacitance thus is equal $1.4 \times 10^{-19}$ $S^2$. Depending on the number of turns and the stent having an assumed diameter of 8 mm and a length of 40 mm, an inductance of approx. $4 \times 10^{-6}$ Vs/A results. The resulting surface of a plate capacitor with a relative dielectric constant of 2 and a distance of 0.1 mm between the individual plates is approximately 0.2 $mm^2$. Such a small surface of a plate capacitor is easily realized in a stent. With stronger magnetic fields, that is, frequencies, the resulting surface of a plate capacitor can be further reduced to 0.014 $mm^2$.

Figure 6:
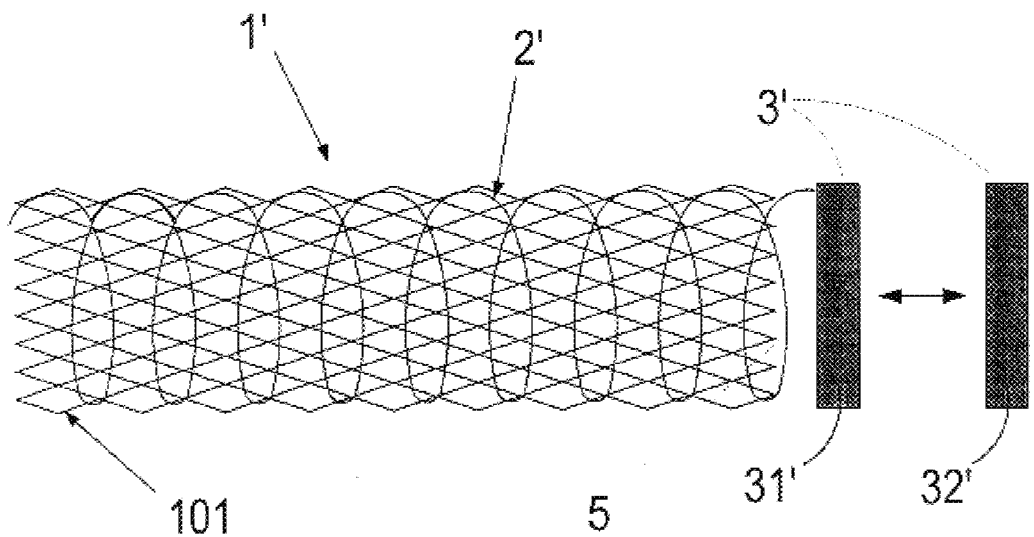
FIG. 6 schematically shows a stent according to the invention with an integrated coil.

FIG. 6 depicts an alternative exemplary embodiment of a stent 1', that forms an inductor 2' and a capacitor 3'. The inductance here is provided in the form of a helix shaped coil 5 that is not formed by the skeleton of the stent itself, but is an additional wire woven into the stent skeleton 101. In this exemplary embodiment, the stent function and the coil function are separated.

The coil 5 is again connected to a capacitor 3' to form a resonance circuit that is either also a separate component or, alternatively, realized by adjacent coil turns or integrated surfaces of the stent.

In applications of the stent, the coil 5, together with the stent material 101 having a smaller radius, is wound onto an application instrument such as a catheter and expands at the site of the application together with the stent material 101 to the desired diameter. Here the wire, that is, the coil 5, preferably is provided with a shape memory or the wire, that is, the coils 5, is/are preloaded on the application instrument.

The intersection surface or the distance of the two capacitor plates of the capacitor 3' is again made adjustable to set the resonance frequency of the resonance circuit. However, it is definitely within the framework of the invention that an adjustment to the resonance frequency can take place in a different form or manner than described above.

Figure 7:
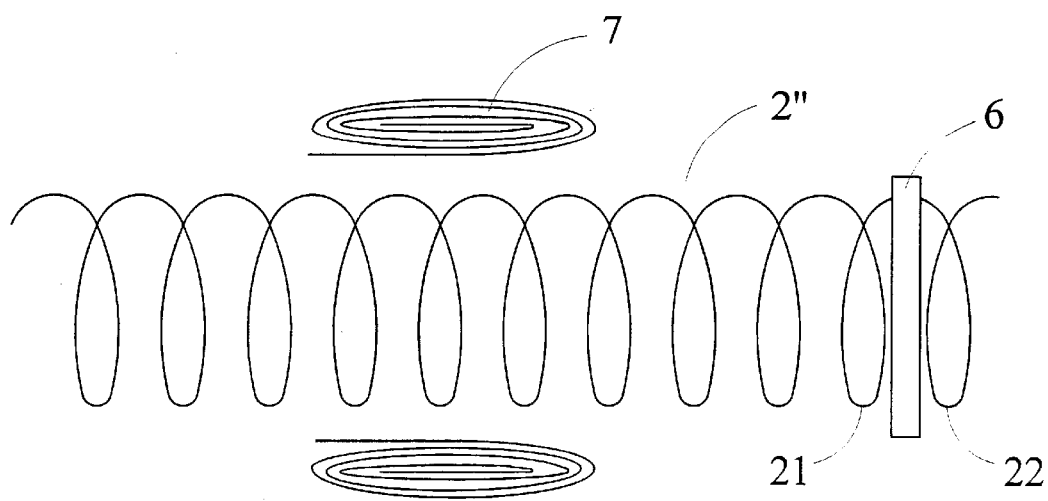
FIG. 7 shows a stent according to the invention provided with a second inductance perpendicular to the first inductance.

In the exemplary embodiment of FIG. 7, the inductor 2" of the stent is disclosed schematically. It can be formed either from the stent material (FIG. 3) or as an additional wire (FIG. 6). No individual capacitor is provided in this exemplified embodiment. Two loops 21, 22 of the inductance 2" actually form the capacitor whereby a dielectric 6 with a dielectric constant as high as possible is disposed between the loops 21, 22 for the increase of the capacitance.

In addition to the inductor 2", an additional inductor 7 in the form of a coil pair 7 is provided, whereby its axis is perpendicular to the axis of the inductor 2". The coil pair 7 is, for instance, formed by two spiral shaped coil arrangements that are integrated into the skeleton of the stent. This assures that in any arrangement of the stent in the tissue, one component is perpendicular to the direction of the field of the homogenous outer magnet. As an alternative to this arrangement, an additional inductance is provided vertical to the two depicted inductances. This assures an increased spin excitation in the observed region in every arrangement of the stent in the magnetic field.

Figure 2E:
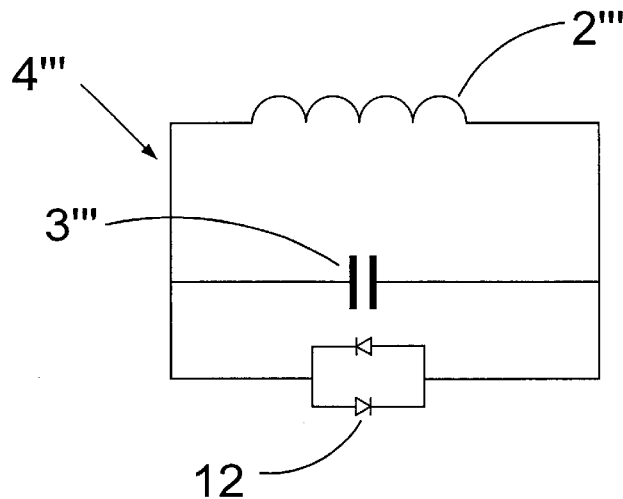
Figure 2F:
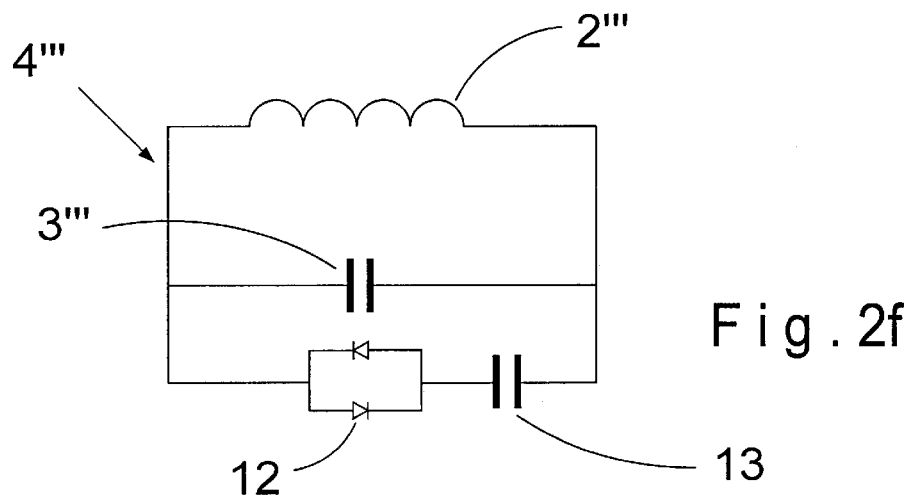

Two additional variants of the invention are disclosed in the diagrams of FIGS. 2e, and 2f. In FIG. 2e the capacitor 3''' is short circuited during the excitation phase by means of two crossed diodes 12 that are provided as additional elements in the skeleton of the stent. The diodes 12 have a conducting-state voltage of approximately 1 Volt, that is, by all means below the voltage produced by the application of high-frequency radiation which usually is above 1 Volt. The diodes 12 thus are conductive by the application of high-frequency radiation to the extent that the capacitor 3''' is short circuited in the excitation phase, and thus no resonance circuit is formed.

This means, in contrast to the previous exemplary embodiments, that no increased local excitation of the nuclear spins takes place while applied by high-frequency radiation. However, when measuring the signal response of the region detected by the inductance 2''', the short circuit of the capacitor 3''' is canceled again. For this purpose, the diodes 12 are formed such, that the conducting-state voltage is above the voltage produced during the spin signal response. Thus, the capacitor 3''' is not short circuited during the emission of magnetic resonance response signals of the atomic nuclei, and a resonance circuit 4''' is formed that effects an amplification of the emitted magnetic resonance response signals of the protons and thus changes the measured signal response.

The diodes 12 may be realized various ways in the stent skeleton. In particular separate components may be used or the diodes may be formed by or in cooperation with the stent material, such as structures applied to the stent skeleton.

With structures that are in principle the same as those disclosed in FIG. 2e, the capacitor 3''' in FIG. 2f is not short circuited, but the resonance circuit 4''' is only detuned in the excitation phase by connecting an additional capacitor 13, such that an amplified excitation of the nuclear spins takes place to a limited degree only. During the emission of magnetic resonance response signals the diodes 12 lock to the extent that the resonance circuit 4''' is not detuned now and an amplification of the emitted magnetic resonance response signals takes place, which results in a changed signal response that is imaged in the magnetic resonance image.

Figure 2G:
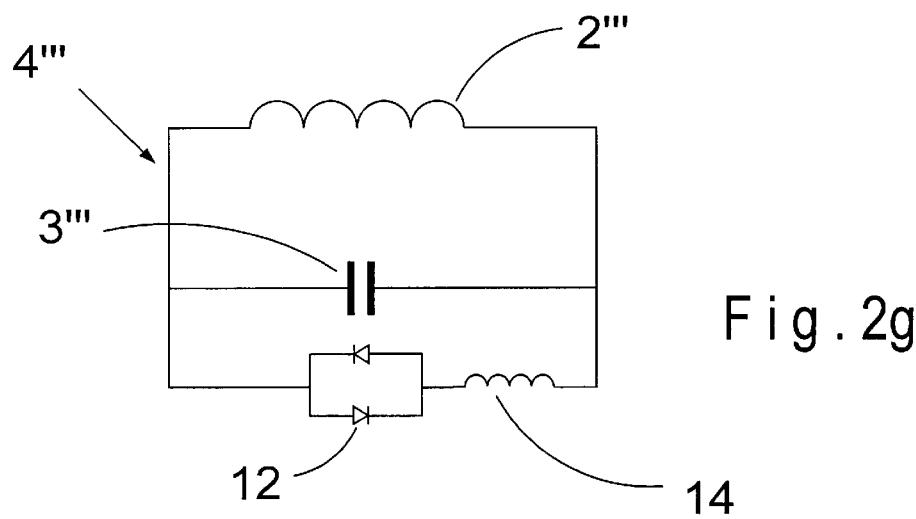

In FIG. 2g the resonance circuit 4''' is not detuned by connecting a capacitor but by connecting a coil 14.

In a further development of the invention, it is possible to also determine the flow velocity of blood flowing through the apparatus. Basically known sequence techniques are here applied. For instance, saturation impulses are applied to the area of blood-supplying tissue, whereby a variation of either the location of the saturation impulses or the time difference between saturation pulse and the small angle excitation allow for the computation of flow velocity and thus for functional information regarding the status of the vessel. Any known methods of flow determination are applicable in connection with the stent according to the invention. New sequence techniques may specifically exploit the characteristics of the stent, that is, an amplified excitation and an amplified reception or simply an amplified reception of the area surrounded by the stent.

Figure 8:
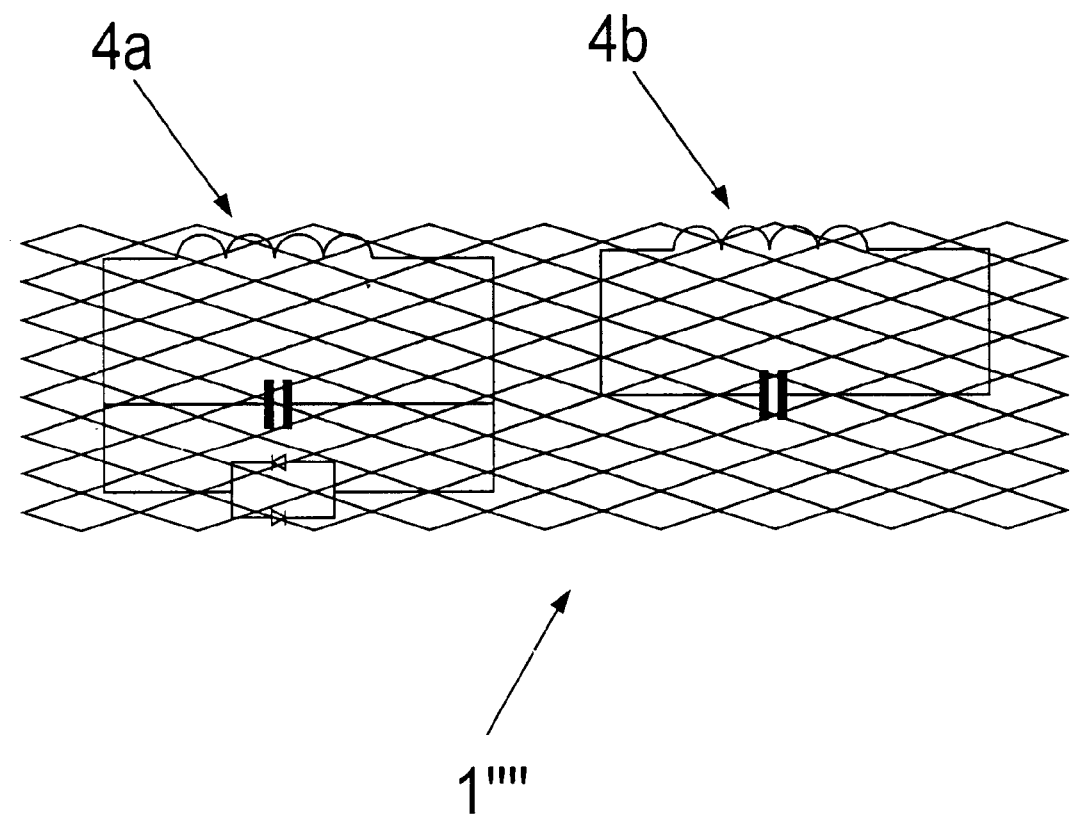
FIG. 8 shows a stent according to the invention with two resonance circuits disposed behind each other.

FIG. 8 shows a stent 1'''' that is preferably used in flow measurements. The stent has two resonance circuits 4a, 4b disposed following each other which are schematically shown. The resonance circuits 4a, 4b may be formed from the stent material or from additional components as described by means of the above cited exemplified embodiments. One resonance circuit 4a is provided with two crossed diodes in accordance with FIG. 2e, such that the capacitor is short circuited during excitation. The other resonance circuit is formed without diodes.

The result is that during application of high-frequency magnetic resonance excitation impulses, amplified excitation takes place in partial areas of the stent, namely the partial area that is surrounded by the resonance circuit 4b without diodes. However, with regard to the surrounding tissue, a changed signal response now exists in the other partial area that is surrounded by resonance circuit 4a as was disclosed by means of FIG. 2e. With the application of suitable sequence techniques, such an arrangement is particularly effective for the determination of flow and thus for the functional control of the stent.

In a further development of the invention (not depicted), a catheter or balloon is equipped with a receptor coil apparatus. Instead of, or in addition to, an external receptor coil of the magnetic resonance system, the catheter or the balloon receives the signal amplified by the stent and transmits it extracorporeally. The catheter may be provided with the same or similar arrangement of inductor, capacitor and diodes and amplify the signals of the stent and transmit them by means of electrically conductive lands or by optical couplings and glass fibers extracorporeally to the tomograph. In comparison with the use of external receptor coils, this variant is characterized by improved signal detection.

In a further development of the invention (not depicted), provisions made that the inductance of the stent itself is used as a receptor coil for the acquirement of magnetic resonance response signals, whereby the inductance is connected via cable connection to extracorporeal function components. It becomes possible to use the inductance of the resonance circuit complementary active for the imaging. Due to the necessity of a cable connection to extracorporeal function components, this in general will only be possible during the implantation of a stent.

The invention is not limited in its embodiment to the previously disclosed exemplified embodiments. It is essential for the invention only that the stent be provided with at least one passive resonance circuit with an inductor and a capacitor.

What is claimed is:

1. A magnetic resonance imaging process for the imaging and determination of the position of a stent introduced into an examination object, the process comprising the steps of:

placing the examination object in a magnetic field, the examination object having a stent with at least one passive resonance circuit disposed therein;

applying high-frequency radiation of a specific resonance frequency to the examination object such that transitions between spin energy levels of atomic nuclei of the examination object are excited; and detecting magnetic resonance signals thus produced as signal responses by a receiving coil and imaging the detected signal responses;

wherein, in a locally defined area proximate the stent, a changed signal response is produced by the at least one passive resonance circuit of the stent, the passive resonance circuit comprising an inductor and a capacitor forming a closed-loop coil arrangement such that the resonance frequency of the passive resonance circuit is essentially equal to the resonance frequency of the applied high-frequency radiation and such that the area is imaged using the changed signal response.

2. The process according to claim 1, wherein the application of the high-frequency radiation comprises the step of exciting the resonance circuit to obtain an amplified excitation of the nuclear spins of the examination object in the locally defined area.

3. The process according to claim 2, wherein the step of exciting is performed such that the locally defined area where the amplification of the excitation of the nuclear spins takes place is located within the stent.

4. The process according to claim 1 wherein with the step of the application of the high-frequency radiation further causes the resonance circuit to become at least one of a detuned circuit and a short circuited circuit to the extent that no amplified excitation of the nuclear spins takes place in the locally defined area.

5. The process according to claim 1, comprising the steps of at least one of forming and activating the resonance circuit at the stent only after insertion of the stent into the examination object.

6. The process according to claim 5, comprising the step of forming the resonance circuit by unfolding the stent during its application.

7. The process according to claim 6, comprising the step of forming a second passive resonance circuit on the stent.

8. The process according to claim 1, comprising the step of facilitating resonant tuning of the resonance circuit by adjusting at least one of the inductor and the capacitor.

9. The process according to claim 8, comprising the step of forming a second passive resonance circuit on the stent.

10. A stent imageable by a magnetic resonance imaging system and having a skeleton which can be unfolded, the stent comprising at least one passive resonance circuit having an inductor and a capacitor forming a closed-loop coil arrangement and whose resonance frequency corresponds to a resonance frequency of high-frequency radiation applied by the magnetic resonance imaging system.

11. The stent according to claim 10, wherein the skeleton of the stent acts as the inductor.

12. The stent according to claim 11, wherein the skeleton is comprised of a material having at least one layer which is highly conductive.

13. The stent according to claim 12, wherein the stent material comprises at least two layers, at least one layer having high conductivity and at least one layer having low conductivity.

14. The stent according to claim 13, wherein the layer having high conductivity is separated at plural locations to define plural mutually insulated areas of the skeleton so as to form an inductor.

15. The stent according to claim 13, wherein the skeleton comprises a honey-comb structure which is separated regularly above and beneath crossing points thereof.

16. The stent according to claim 15, wherein the skeleton of the stent is configured as one of a helix, a double helix and multiple helixes.

17. The stent according to claim 12, wherein the layer having high conductivity is separated at plural locations to define plural mutually insulated areas of the skeleton so as to form an inductor.

18. The stent according to claim 10, wherein the inductor of the passive resonance circuit comprises a separate coil which is integrated into the stent.

19. The stent according to claim 18, wherein the coil is woven into the skeleton of the stent.

20. The stent according to claim 19, wherein the coil is connected to the skeleton in such a manner that it unfolds together with the skeleton when unfolding the stent.

21. The stent according to claim 20, wherein the inductor comprises parallel conductors that partially act as a capacitor.

22. The stent according to claim 20, wherein the capacitor comprises a separately provided condenser.

23. The stent according to claim 22, wherein the stent comprises a detuning circuit for detuning the resonance circuit when applying the high-frequency radiation.

24. The stent according to claim 23, wherein the detuning circuit comprises a condenser which is switchable parallel to the capacitor of the resonance circuit with the application of high-frequency radiation.

25. The stent according to claim 24, wherein the switch circuit comprises two diodes which are switchable parallel to the capacitor.

26. The stent according to claim 25, further comprises a switch coupled to activate or deactivate at least one resonance circuit.

27. The stent according to claim 26, wherein at least one of the inductor and the capacitor of the resonance circuit are adjustable for the tuning of the resonance frequency of the magnetic resonance imaging system.

28. The stent according to claim 27, wherein when a change in geometry of the stent occurs during its deployment, a product of the inductor and the capacitor of the resonance circuit remains approximately constant.

29. The stent according to claim 28, wherein the resonance circuit has a low quality (Q factor), such that a broad frequency response is provided.

30. The stent according to claim 29, wherein the resonance circuit has plural parallel switched inductors.

31. The stent according to claim 29, wherein the resonance circuit has plural serially switched inductors.

32. The stent according to claim 29, wherein the resonance circuit has plural parallel switched capacitors.

33. The stent according to claim 29, wherein the resonance circuit has plural serially switched capacitors.

34. The stent according to claim 23, wherein the detuning circuit comprises a coil which is switchable parallel to the inductance of the resonance circuit with the application of high-frequency radiation.

35. The stent according to claim 22, further comprising a switch circuit coupled to short circuit the capacitor when applying the high-frequency radiation.

36. A magnetic resonance imaging method for the imaging and determination of the position of a stent with a foldable skeleton introduced into an examination object, the method comprising:

arranging the examination object in an external magnetic field, the examination object having a stent including at least one passive resonance circuit formed in the skeleton of the stent;

applying high-frequency radiation of a specific resonance frequency to the examination object, such that transitions between spin energy levels of atomic nuclei of the examination object are excited;

detecting magnetic resonance signals thus produced as signal responses by a receiving coil, such that, in a locally defined area proximate the stent, one of the signal responses includes a changed signal response produced by the at least one passive resonance circuit, the at least one passive resonance circuit comprising an inductance and a capacitance forming a closed-loop coil arrangement wherein the resonance frequency of the passive resonance circuit is approximately equal to the resonance frequency of the applied high-frequency radiation; and imaging the produced signal responses in spatial resolution, such that, the locally defined area proximate the stent is imaged using the changed signal response produced.

37. The method of claim 36 wherein the application of the high-frequency radiation further comprises exciting the resonance circuit to obtain an amplified excitation of the nuclear spins of the examination object in the locally defined area.

38. The method according to claim 37 wherein the step of exciting is performed such that the locally defined area where the amplification of the excitation of the nuclear spins takes place is located within the stent.

39. The method of claim 36 wherein the application of the high-frequency radiation causes the resonance circuit to become detuned or have the capacitance short circuited to the extent that no amplified excitation of the nuclear spins takes place in the locally defined area, such that when measuring of the signal response of the locally defined area the detuning of the resonance circuit or the short circuiting of the capacitance is canceled, thereby resulting in a change in the signal response.

40. The method of claim 36 further comprising adjusting the resonance frequency of the resonance circuit at the stent by unfolding of the stent after insertion of the stent into the examination object.

41. The method of claim 40 further comprising forming a second resonance circuit on the stent, such that coils of respective inductances of the said resonance circuit and the second resonance circuit are aligned vertically to each other.

42. The method of claim 40 further comprising forming a second resonance circuit on the stent, such that coils of respective inductances of the said resonance circuit and the second resonance circuit are aligned behind each other.

43. The method of claim 36 further comprising adjusting at least one of the inductance and the capacitance for resonant tuning of the resonance circuit.

44. A stent imageable by a magnetic resonance imaging system and having a skeleton which can be unfolded, the stent comprising at least one passive resonance circuit having an inductance and a capacitance forming a closed-loop coil arrangement and whose resonance frequency corresponds to a resonance frequency of high-frequency radiation applied by the magnetic resonance imaging system;

wherein the skeleton of the stent is one of the inductance and integrated with the inductance, such that when the stent unfolds, the skeleton of the stent and the inductance unfold.

45. The stent of claim 44 wherein the skeleton of the stent acts as the inductance.

46. The stent of claim 45 wherein the skeleton includes a material having at least one layer which is highly conductive so as to form the inductance.

47. The stent of claim 46 wherein the material includes at least two layers, at least one layer having high conductivity and at least one layer having low conductivity.

48. The stent of claim 47 wherein the layer having high conductivity is separated at plural locations to prescribe plural mutually insulated areas of the skeleton.

49. The stent of claim 47 wherein the skeleton includes a honey-comb structure having a conductive layer that is separated regularly above and beneath crossing points of the honey-comb structure.

50. The stent of claim 49 wherein the skeleton of the stent is configured as one of a helix, a double helix and multiple helixes.

51. The stent of claim 46 wherein the layer having high conductivity is separated at plural locations to prescribe plural mutually insulated areas of the skeleton.

52. The stent of claim 44 wherein the inductance is integrated into the skeleton of the stent.

53. The stent of claim 44 wherein the inductance of the resonance circuit is defined by a separate coil of the resonance circuit which is integrated in the stent.

54. The stent of claim 53 wherein the separate coil is connected to the skeleton in such a manner that it unfolds together with the skeleton when the stent is unfolded.

55. The stent of claim 54 wherein the capacitance is at least partially formed by two loops of the inductance in which a dielectric is arranged between the two loops.

56. The stent of claim 55 wherein the capacitance is formed by a separately provided at least one of a plate condenser and a cylinder condenser.

57. The stent of claim 56 wherein the stent comprises a detuning circuit for detuning the resonance circuit when applying the high-frequency radiation.

58. The stent of claim 57 wherein the detuning circuit comprises a condenser which is switchable parallel to the capacitance of the resonance circuit with the application of high-frequency radiation.

59. The stent of claim 58 wherein the switch circuit comprises two diodes which are switchable parallel to the capacitance.

60. The stent of claim 59 further comprises a switch coupled to one of activate and deactivate at least one resonance circuit.

61. The stent of claim 60 wherein at least one of the inductance and the capacitance of the resonance circuit are adjustable for the tuning of the resonance frequency of the magnetic resonance system.

62. The stent of claim 61 wherein when a change in geometry of the stent occurs during its application, a product of the inductance and the capacitance of the resonance circuit remains approximately constant, such that an amplification of the inductance accompanies a decrease in capacitance.

63. The stent of claim 62 wherein the resonance circuit is low quality.

64. The stent of claim 63 wherein the resonance circuit has plural parallel switched inductors.

65. The stent of claim 63 wherein the resonance circuit has plural serially switched inductors.

66. The stent of claim 63 wherein the resonance circuit has plural parallel switched capacitors.

67. The stent of claim 63 wherein the resonance circuit has plural serially switched capacitors.

68. The stent of claim 63 wherein the stent has several resonance circuits with several inductances aligned vertical to each other.

69. The stent of claim 63 wherein the stent has several resonance circuits with several inductances arranged behind each other.

70. The stent of claim 57 wherein the detuning circuit comprises a coil which is switchable parallel to the inductance of the resonance circuit with the application of high-frequency radiation.

71. The stent of claim 56 further comprising a switch circuit coupled to short circuit the capacitance when applying the high-frequency radiation.

* * * * *

UNITED STATES PATENT AND TRADEMARK OFFICE
CERTIFICATE OF CORRECTION

PATENT NO. : 6,280,385 B1
DATED : August 28, 2001
INVENTOR(S) : Andreas Melzer and Martin Busch It is certified that error appears in the above-identified patent and that said Letters Patent is hereby corrected as shown below:

<u>Title page,</u>
Item [56], References Cited, U.S. PATENT DOCUMENTS, insert the following references:

```
-- 3,731,184  *  5/1973    Goldberg et al. . .
   4,815,473  *  3/1989    Watson et al. . .
   5,178,618  *  1/1993    Kandarpa . . .
   5,744,958  *  4/1998    Werne . . .
   5,964,705  * 10/1999    Truwit et al. . .
   5,967,986  * 10/1999    Cimochowski et al. . . . --
```

<u>Column 1,</u>
Line 20, after "frequency" insert -- is --.
Line 38, after "field in" insert -- the --.
Line 64, replace "p. 461–493" with -- pp. 461–493 --.

<u>Column 3,</u>
Lines 11-12, replace "an magnetic" with -- a magnetic --.

<u>Column 4,</u>
Line 31, replace "places" with -- place --.
Line 44, replace "was in particular found" with -- was, in particular, found --.

<u>Column 5,</u>
Line 50, before "form" insert -- the --.

<u>Column 7,</u>
Lines 13-14, replace "Ultrasound examination are" with -- Ultrasound examination is --.
Line 42, delete "of the" (second occurrence).
Line 56, replace "that is" with -- that it --.

UNITED STATES PATENT AND TRADEMARK OFFICE
CERTIFICATE OF CORRECTION

PATENT NO. : 6,280,385 B1
DATED : August 28, 2001
INVENTOR(S) : Andreas Melzer and Martin Busch It is certified that error appears in the above-identified patent and that said Letters Patent is hereby corrected as shown below:

Column 8,
Line 37, replace "excitation of 20" with -- excitation of 2° --.

Column 9,
Line 42, replace "consist" with -- consists --.

Signed and Sealed this

First Day of April, 2003

JAMES E. ROGAN
*Director of the United States Patent and Trademark Office*